United States Patent [19]

Gotoh et al.

[11] 4,124,634

[45] Nov. 7, 1978

[54] PROCESS FOR PRODUCING METHACRYLIC ACID FROM ISOBUTYLENE BY TWO STEP OXIDATION

[75] Inventors: Isao Gotoh; Junji Endoh, both of Yokohama; Tohru Ueno, Hatano, all of Japan

[73] Assignee: Asahi Glass Company, Ltd., Tokyo, Japan

[21] Appl. No.: 775,427

[22] Filed: Mar. 8, 1977

Related U.S. Application Data

[63] Continuation of Ser. No. 624,646, Oct. 22, 1975, abandoned.

[30] Foreign Application Priority Data

Oct. 23, 1974 [JP]  Japan .................................. 49-121510

[51] Int. Cl.$^2$ ...................... C07C 45/04; C07C 51/32
[52] U.S. Cl. ................................ 562/532; 260/604 R; 562/535
[58] Field of Search ........... 260/530 N, 604 R, 533 N

[56] References Cited

U.S. PATENT DOCUMENTS

| 3,725,472 | 3/1973 | Kowano et al. ................. 260/530 N |
| 3,882,047 | 5/1975 | Nuna et al. ...................... 260/530 N |

FOREIGN PATENT DOCUMENTS 939,713  10/1963  United Kingdom ................ 260/530 N

*Primary Examiner*—Vivian Garner
*Attorney, Agent, or Firm*—Oblon, Fisher, Spivak, McClelland & Maier

[57] ABSTRACT

In a process for producing methacrylic acid by two step oxidation comprising a first oxidation step of producing methacrolein by reacting isobutylene with molecular oxygen in the presence of a diluent gas and a catalyst, and a second oxidation step of producing methacrylic acid by reacting methacrolein with molecular oxygen in the presence of a diluent gas and a catalyst, the improvement comprises using nitrogen as the diluent gas in the first oxidation step and nitrogen and steam as the diluent gas in the second oxidation step, mixing the reaction products obtained in the first and second oxidation steps, separating and recovering methacrolein and methacrylic acid from the mixture and feeding the recovered methacrolein back into the second oxidation step as a starting material.

8 Claims, 1 Drawing Figure

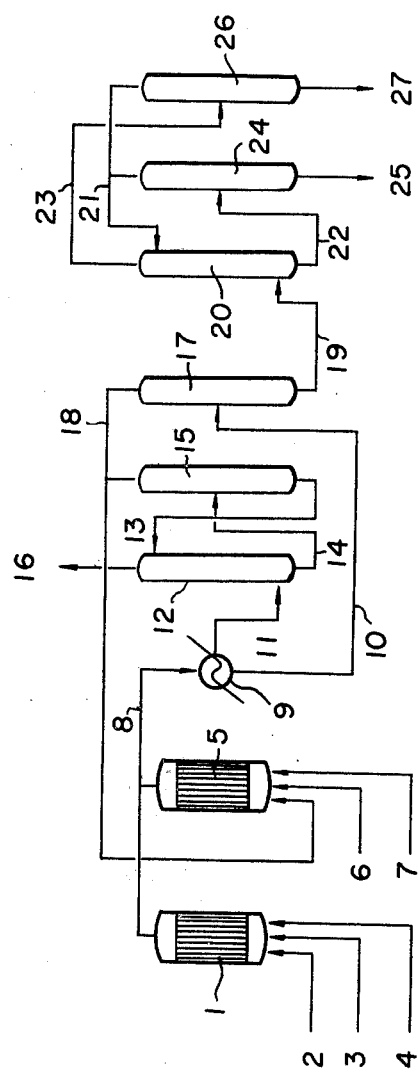

PROCESS FOR PRODUCING METHACRYLIC ACID FROM ISOBUTYLENE BY TWO STEP OXIDATION

This is a continuation of application Ser. No. 624,646, filed Oct. 22, 1975, now abandoned.

BACKGROUND OF THE INVENTION

1. Field of the Invention

The present invention relates to a process for producing methacrylic acid from isobutylene. More particularly, it relates to a novel process for producing methacrylic acid from isobutylene by a two step oxidation consisting of a first step of oxidizing isobutylene to methacrolein and a second step of oxidizing methacrolein to methacrylic acid.

2. Description of the Prior Art

Heretofore, it has been known to produce methacrylic acid by reacting isobutylene with molecular oxygen in the presence of a diluent gas and steam. However, a catalyst suitable for industrial production of methacrylic acid from isobutylene in high yield, has not been found. Accordingly, it is industrially advantageous to conduct the reaction in two steps using a desirable catalyst for production of methacrolein from isobutylene and a desirable catalyst for production of methacrylic acid from methacrolein.

However, when methacrylic acid is produced in such a two step oxidation, it is relatively difficult to attain high selectivity of methacylic acid in the second oxidation step if the conversion of methacrolein is high. That is, the selectivity of methacrylic acid formation decreases with increasing conversion of methacrolein. Accordingly, it becomes advantgeous to conduct the second oxidation step under conditions such that the conversion of methacrolein is relatively low and then to recover the unreacted methacrolein from the reaction products and recycle them back into the second oxidation step. The unreacted methacrolein is separated from the reaction products in the second oxidation step while the object product, methacrylic acid is recovered. This is accomplished by cooling the reaction products in the second oxidation step to liquefy them, and/or further contacting them with water to separate the gaseous components of oxygen, nitrogen, carbon dioxide gas and the like. As a result, a liquid phase containing methacrolein and/or methacrylic acid, is obtained and these are separated by distillation.

However, the present inventors have determined that in many cases a dangerous self-explosive gas is formed in the process of recovering the products of the second oxidation step. The self-explosive gas includes self-flammable gas, usually called a detonating gas. The present inventors have further determined that the explosive gas is apparently formed by the following mechanism. The methacrolein in the reaction product has a relatively low boiling point and a low solubility in water. As a result, it is relatively difficult to recover a high proportion of the methacrolein in the liquid phase during the recovery process, because it is so insoluble. However, the methacrylic acid and steam in the reaction product can be easily recovered in the liquid phase. Accordingly, during the recovery process, methacrolein remains present in the gaseous system of oxygen, nitrogen and carbon dioxide gas of the reaction product.

Furthermore, the conversion of methacrolein in the second oxidation step is relatively low because of the characteristics of the catalyst. The consumption of oxygen is correspondingly small and a large amount of oxygen remains in the reaction product. Accordingly, the overall composition of the methacrolein-containing gas formed in the recovery process becomes explosive. In order to prevent this formation of an explosive gas, decreasing the supply of oxygen while increasing the supply of nitrogen used as a diluent gas has been suggested. Unfortunately, in this method, the resultant conditions are far from those which are optimum for catalyst performance in the second oxidation step, whereby the yield of the object product in the second oxidation step is disadvantageously decreased. Consequently, there remains a need for an improvement in the two step oxidation preparation of methacrylic acid.

SUMMARY OF THE INVENTION

Accordingly, it is an object of the present invention to provide a process for producing methacrylic acid from isobutylene which maintains optimum conditions for the performance of the catalyst in the second oxidation step and prevents the formation of an explosive gas during the process for recovering the unused methacrolein and the desired methacrylic acid from the reaction product, thereby enabling safe separation of these products.

It is another object of the invention to provide a process for producing methacrylic acid from isobutylene wherein methacrolein and methacrylic acid are effectively separated and recovered from the reaction products in the first and second oxidation steps.

It is still another object of this invention to provide a process for producing methacrylic acid from isobutylene which includes separating and recovering methacrolein and methacrylic acid from the reaction products in the first and second oxidation steps while preventing their polymerization.

It is a further object of this invention to provide a process for producing methacrylic acid from isobutylene wherein methacrolein and methacrylic acid are respectively produced in high yield in the first and second oxidation steps.

These and other objects of this invention as will hereinafter become clear from the ensuing discussion have been attained by providing a process for producing methacrylic acid from isobutylene by a two step oxidation consisting of first oxidizing isobutylene to methacrolein and then oxidizing methacrolein to methacrylic acid, wherein nitrogen is used as a diluent gas in the first oxidation step and nitrogen and steam are used as a diluent gas in the second oxidation step, and the reaction products of the first and second oxidation steps are mixed and methacrolein and methacrylic acid are separated and recovered from the mixture of their reaction products and the recovered methacrolein is recycled as a starting material into the second oxidation step.

BRIEF DESCRIPTION OF THE DRAWING

A more complete appreciation of the invention and many of the attendant advantages thereof will be readily attained as the same becomes better understood by reference to the following detailed description when considered in connection with the accompanying drawings, wherein:

FIG. 1 is a flow diagram of one embodiment of an apparatus used for the process of this invention.

DETAILED DESCRIPTION OF THE PREFERRED EMBODIMENTS

Referring to FIG. 1, one embodiment of the process of this invention will be illustrated. In the specification, the terms "conversion" and "selectivity" have the following meanings.

| | | | | |
|---|---|---|---|---|
| Conversion | = | Converted component (moles) | ÷ Fed component (moles) | X100. |
| Selectivity | = | Resulting product (moles) | ÷ Converted component (moles) | X100. |

The first and second oxidation steps in the process of this invention can be operated as follows. The first oxidation step involves oxidizing isobutylene 3 with molecular oxygen 4 in the presence of a diluent gas 2 and a catalyst (not shown) in a reactor 1. Nitrogen in air is used as the diluent gas 2. However, if desired, it is possible to utilize other suitable diluent gases such as carbon dioxide, helium, steam, and the like, which do not interfere with the effect of this invention. The molecular oxygen 4 can be supplied from any conventional source for providing molecular oxygen under the conditions of the reaction. It is preferred to use air since it is economical and also is the source of the diluent gas.

The concentration, of isobutylene to be used as the starting material is preferred to be less than 4 mole % from the viewpoint of temperature control. The molar ratio of molecular oxygen to isobutylene is preferred to be in the range of 1/3 – 4/1, especially 1/1 – 3/1. The amount of diluent gas in the feed gas is preferred to be in the range of 50 – 97 mole % especially 65 – 90 mole %. It is necessary that the diluent gas contain more than 30 mole % preferably more than 50 mole %, of a gas which is not condensed in the subsequent recovery process. When air is used as the source of molecular oxygen, nitrogen, which is a diluent gas and is not condensed in the subsequent recovery process, can be supplied in amounts corresponding to the composition of air. That is, the amount of nitrogen in air is sufficient for use as the diluent gas. Accordingly, it is preferred to use air as the source of molecular oxygen.

Suitable catalysts for use in the first oxidation step include metal oxides and other conventional catalysts which can be supported by carriers such as silica, alumina, silicon carbide, molecular sieve and the like. Such suitable catalysts include molybdenum-antimony oxides, molybdenum-tellurium oxides, molybdenum-bismuth oxides and antimony-iron oxides or mixtures thereof with copper, phosphorus, cobalt, niobium or tantalum. The reaction can be conducted by using the above-mentioned starting gases and catalyst in a continuous type, batch type, fixed-bed type or fluidized-bed type reactor. The reaction temperature is preferred to be in the range of 200° – 500° C, especially 250° – 450° C. The pressure is preferred to be in the range of 0.5 – 10 atm, especially 1 – 3 atm. The apparent contact time for the reaction is preferred to be in the range of 0.1 – 20 seconds, especially 1 – 10 seconds. In the first oxidation step of this invention, it is preferred to achieve a conversion of isobutylene higher than 80%, especially higher than 90%. In this use, methacrolein can be produced in a high selectivity of 80 – 90%.

In the second oxidation step, the conditions are substantially the same as those of the first oxidation step except for the following. In the case of the second oxidation step conducted in a reactor 5, it is necessary to include steam in the diluent gas 6 containing nitrogen gas so as to increase the yield of the resultant methacrylic acid. The amount of the diluent gas 6 in the feed gas should be in the same range as in the first oxidation step. It is preferred to have 5 – 90 mole %, especially 15 – 75 mole %, of steam in the feed gas. It is also possible to add other diluent gases as in the first oxidation step. The amount of molecular oxygen 7 fed in the second oxidation step should be in the range of 1.2 – 2.0 moles, especially 1.5 – 1.8 moles, for 1 mole of methacrolein in order to maintain a good activity of the catalyst. It is preferred to use air as the source of the molecular oxygen, for the process of the invention because thereby nitrogen gas is also supplied in a sufficient amount to be used as the diluent gas for the oxidation. Suitable catalysts for use in the second oxidation step include the metal oxides used in the first oxidation step, and also molybdenum-thallium oxides. Oxides with rhenium, copper, cobalt, vanadium or mercury added if desired; molybdenum-phosphorus oxides with an oxide of vanadium, antimony, arsenic, aluminum, or cobalt added, if desired; molybdenum-palladium oxides with an oxide of antimony, or arsenic added, if desired; phosphomolybdic acid; and an ammonium, bismuth, antimony, potassium, cesium, rubidium or thallium salt of phosphomolybdic acid, which has a central phosphorus atom and a ligand of molybdenum. Suitable reaction temperatures and pressures for the second oxidation step are substantially in the same range as those of the first oxidation step. In the second step, in order to increase the selectivity of methacrylic acid, the conversion of methacrolein should be less than 80%, preferably in the range of 40 – 70%, because of the characteristics of the catalyst. In this manner, the selectivity of methacrylic acid is kept as high as 65 – 85%. The first and second oxidation steps should be conducted according to the above-mentioned parameter limitations.

In the process of this invention, it is characteristic that the reaction products in both the first and second oxidation steps are mixed 8 as shown in FIG. 1, whereby methacrylic acid can be smoothly recovered in high yield without formation of an explosive gas in the recovery process. According to the comparative tests described below, the possibility of forming an explosive gas in the recovery process for the reaction product of the second step varies depending upon the amount of oxygen fed into the second oxidation system. It has been found that the conversion of methacrolein in the second oxidation step should satisfy the conditions stated in Table 1 in order to prevent formation of the explosive gas. In the following, the amount of oxygen is given as the number of moles per 1 mole of methacrolein.

TABLE 1

| COMPARATIVE TESTS | |
|---|---|
| Amount of oxygen (moles) | Conversion of methacrolein required for preventing formation of explosive gas (%) |
| 0.75 | > 40 |
| 1 | > 50 |
| 1.25 | > 65 |
| 1.5 | > 80 – 90 |

As can be seen from the data of Table 1, the conversion of methacrolein must be higher than 60% when using 1.2 moles of oxygen, the minimum amount preferred for use with the catalyst in the second oxidation step, in order to prevent formation of an explosive gas. It is necessary to have a safety allowance of about 5%. Accordingly, the conversion of methacrolein in the second oxidation step should be more than 65%. Under this condition, it is difficult to attain a high selectivity of methacrylic acid when using the catalyst in the second oxidation step. When the amount of oxygen is higher than 1.5 moles, the conversion of methacrolein should be 80 – 90%, and when the safety allowance is considered, the conversion of methacrolein should be 90 – 100%, which cannot be achieved in practice.

On the other hand, when the reaction products in the first oxidation step are mixed with the reaction products in the second oxidation step according to this invention, the formation of an explosive gas in the recovery process is easily controlled. Even though the amount of oxygen in the reaction system is high, it is possible to utilize a low conversion of methacrolein while obtaining a high selectivity of methacrylic acid. As can be seen from the data in Table 2, the conversion of methacrolein required in the second oxidation step in order to prevent the formation of an explosive gas is greatly decreased with respect to the amount of oxygen, as compared with the comparative test results of Table 1.

TABLE 2

THIS INVENTION

| Amount of oxygen (moles) | Conversion of methacrolein required for preventing formation of explosive gas (%) |
|---|---|
| 1 | > 32 |
| 1.25 | > 44 |
| 1.5 | > 56 |
| 1.75 | > 72 |
| 2 | > 90 |

As Table 2 shows, in accordance with the process of this invention, when using 1.2 moles – 1.8 moles of oxygen for 1 mole of methacrolein, which is the preferred amount for the catalyst in the second oxidation step, the required conversion of methacrolein is less than 80% and generally 40–70%, which is preferred for providing high selectivity of methacrylic acid.

In the process of this invention, the reaction products of the first and second oxidation steps are mixed before cooling the reaction products as shown in FIG. 1. However, it is possible to mix the reaction products during or after cooling depending upon the safety limitations, resulting from the amount of oxygen used and the conversion of methacrolein. The mixture of the reaction products 8 contains methacrolein, methacrylic acid, isobutylene, acetic acid, oxygen, nitrogen, steam, carbon dioxide gas and carbon monoxide in relative amounts depending upon the conditions used in the first and second oxidation steps. The mixture of the reaction products is cooled by any suitable cooling method such as an indirect heat-exchanger 9 at a temperature for liquefying methacrylic acid, and if desirable methacrolein, preferably at 1° – 50° C, especially 5° – 20° C. During the cooling, it is characteristic that methacrylic acid and methacrolein are cooled with steam in the reaction mixture to form a liquid since a large amount of steam is included. When the reaction products are indirectly cooled, i.e., when the reaction products are not contacted with coolant, methacrolein and methacrylic acid are condensed together with steam to form a solution diluted with water. Accordingly, easily polymerized methacrolein and methacrylic acid are not polymerized. The amount of the resultant solution is remarkably small because of this indirect cooling, and, accordingly, effective recovery can be attained. The solution 10 of methacrolein and methacrylic acid diluted with water, which controls the polymerization thereof, can be discharged from the bottom of the heat-exchanger 9.

It has been found that the polymerizations of methacrolein and methacrylic acid can be further controlled by cooling the mixture 8 in two or more cooling steps. According to these studies, methacrolein and methacrylic acid are relatively difficult to polymerize in a gaseous condition even at high temperatures. However, they are easily polymerized, with attendant loss, when they are kept at a high temperature in a liquefied condition. Accordingly, when the mixture 8 of the reaction products is suddenly cooled, part of the methacrolein and methacrylic acid is condensed during the cooling operation, thereby being kept at a high temperature is a liquefied condition. The tendency is especially high in the case of methacrylic acid which has a high boiling point and is easily liquefied. Accordingly, the cooling operation is preferably conducted in multistages, such as in 2 – 3 steps. In such a case where the cooling operation is conducted in at least two steps, in the first step, the mixture of the reaction products is cooled to a temperature which prevents condensation of methacrolein and methacrylic acid, preferably 120° – 170° C. In the second step, the mixture is cooled to 1° – 50° C which is finally required by this invention. The second step of the cooling operation can also be conducted in multi-steps, if desired. In accordance with such a multi-step cooling operation, the amount of polymerization is decreased. The cooling methods to be employed depend upon the cooling temperatures involved. For example, a cooling method using water can be used in high temperature systems and a cooling method using a desirable coolant, e.g., aqueous solutions of inorganic salts, glycols, alcohols, and the like can be used in low temperature systems.

The gaseous components 11 including those components having low boiling points and sparingly soluble in water which are separated by the heat-exchanger 9, can be discharged without recovery if the content of methacrolein is small. However, it is customary to feed the gaseous components 11 into an absorption tower 12 to contact them with water 13, whereby the water soluble methacrolein is selectively absorbed and dissolved in water. The absorbed solution 14 is distilled by a distillation tower 15 to recover methacrolein. The water discharged from the distillation tower 15 can be recycled to the absorption tower 12. The gaseous components which are not absorbed in water are discharged as an exhaust gas 16. In the conventional process, there is a possibility of forming an explosive gas in the absorption tower 12 by decreasing the concentration of methacrolein in the gaseous components when contacting them with water.

However, according to the process of this invention, the formation of the explosive gas is prevented.

When methacrolein and methacrylic acid are separated and recovered from the liquefied components 10 discharged from the heat-exchanger 9, the liquefied components can be directly distilled. However, an amount of water 7 – 70 times (molar ratio) that of the methacrylic acid is included in the liquefied component. Accordingly, it is necessary to distill the water. This is not advantageous for efficiency, and furthermore, the products are azeotropically distilled with the water.

Accordingly, before the liquefied components are distilled, it is preferred to separate the water from the liquefied components as much as possible by any suitable conventional method. Such methods include the extraction method of extracting methacrolein and methacrylic acid by using a desirable extracting reagent such as aliphatic or aromatic hydrocarbons, halohydrocarbons, ketones and the like; and the salting-out method of separating methacrolein and methacrylic acid from water by adding a desirable salting-out agent such as water soluble inorganic acids or inorganic salts. In accordance with these methods, methacrolein and methacrylic acid can be separated in high efficiency by distilling a solution having a relatively low content of water.

FIG. 1 shows one preferred embodiment using an extracting reagent, wherein the solution 10 is fed to a distillation tower 17 to distill methacrolein 18 having a low boiling point whereby methacrolein is separated and recovered. A small amount of water is included in the recovered methacrolein. This is preferred for use as the starting material for second oxidation step because the reaction for producing methacrylic acid is conducted in the presence of water. However, if necessary, a purified product can be obtained by removing water and the other impurities. The components having high boiling points 19 discharged from the distillation tower 17 are fed to the extraction tower 20 wherein the components are contacted with an extracting reagent 21 such as water insoluble organic solvents e.g., aliphatic or aromatic hydrocarbons, halohydrocarbons, esters, and the like, whereby the water phase 23 is separated from the extraction phase 22 containing methacrylic acid. The extraction phase 22 is fed to the distillation tower 24 and the extracting reagent 21 is separated by distillation to obtain methacrylic acid having a purity of higher than 99% which may contain small amounts of water and organic materials in most cases. On the other hand, the water phase 23 separated by the extraction tower 20 contains acetic acid, and is fed to the distillation tower 26 to separate the extracting reagent 21 from the other components such as acetic acid.

The embodiment for separating and recovering methacrolein and methacrylic acid by mixing the reaction products in the first and second oxidation steps and cooling the mixture to liquefy the component has been illustrated in FIG. 1. However, it is possible to employ other embodiments wherein the reaction products in the first and second oxidation steps are respectively pre-cooled, and then directly contacted with water to have the water soluble components of methacrolein and methacrylic acid absorbed in the water. The water phase is then distilled to separate and recover the products. In this case, the contacting of the reaction products with water is preferably conducted at 1° – 60° C, under a pressure of 1 – 10 atm, at a rate of 1 – 7 kg of water per 1 m$^3$ of the gas. The resulting aqueous solution of methacrolein and methacrylic acid is preferably treated to remove as much of the water as possible by the extraction method or the salt-out method. Thereafter, methacrolein and methacrylic acid are recovered by distillation.

The resulting methacrolein and methacrylic acid can be used as products with or without post treatments. A portion or all of the methacrolein is fed as a starting material for producing methacrylic acid back into the second oxidation step. In the process of this invention, pure methacrolein which does not contain impurities such as unreacted isobutylene, carbon monoxide, carbon dioxide and the like, can be fed into the second oxidation step. According to studies, in this case, the catalytic activity in the second oxidation step can be maintained at a high level for a long-period of time, whereby the yield of methacrylic acid can be kept high. The reason for this is not clear. However, the tendency is very significant and advantageous when catalysts having a high catalytic activity such as potassium, cesium, rubidium or thallium salts of phosphomolybdate having a central phosphorus atom and a ligand of molybdenum are used in the second oxidation step. In accordance with the process of this invention, impurities such as isobutylene, carbon monoxide, carbon dioxide, and the like, are not included in the methacrolein used in the second oxidation step. Accordingly, it is possible to use a more compact apparatus since a need for an increase in the capacity due to the impurities is not present. In accordance with this invention, methacrylic acid can be produced by a two step oxidation in high yield and safety using a compact apparatus without formation of a detonating gas in the recovery process.

A further understanding can be attained by reference to certain specific examples which are provided for purposes of illustration only and are not intended to be limiting. In the examples, the percent of each component refers to mole percent, except where otherwise indicated.

EXAMPLE 1

A feed gas containing 4.0% of isobutylene, 8.0% of oxygen, 30.1% of nitrogen and 57.9% of water (oxygen and nitrogen are fed as air) was used in the first oxidation step. The gas was passed through a reactor made of stainless steel (having a diameter of 1 inch; a length of 1.5 m) which was filled with a catalyst of oxides of metal components: $Mo_{12}Nb_1Te_1Sb_2$ (atomic ratio) supported on silicon carbide (having a diameter of 4 mm) to react it at 430° C with a 5 seconds contact time. The reaction products contained 2.86% of methacrolein, 0.4% of isobutylene, 1.3% of oxygen, 29.9% of nitrogen, 63.2% of water and 3.3% of carbon dioxide. The conversion of isobutylene was 90.0% and the selectivity of methacrolein was 79.4%. On the other hand, a feed gas containing 4.0% of methacrolein, 5.0% of oxygen, 18.8% of nitrogen and 72.1% of water was used in the second oxidation step. The gas was passed through a reactor made of stainless steel (having a diameter of 1 inch and a length of 1.5 m) which was filled with a catalyst of a mixture of antimony phosphomolybdale and oxides of iron and zirconium supported on silicon carbide (having a diameter of 4 mm) to react it at 340° C with a 4 second contact time. The reaction products contained 2.0% of methacrolein, 1.6% of methacrylic acid, 73.4% of water, 2.7% oxygen, 18.7% of nitrogen, 0.9% of carbon dioxide and 0.5% of carbon monoxide. The conversion of methacrolein was 50.0% and the selectivity of methacrylic acid was 80.0%. The reaction products in the first and second oxidation steps were mixed to form a gaseous mixture of reaction products containing 0.2% of isobutylene, 2.4% of methacrolein, 0.9% of methacrylic acid, 69.1% of water, 2.1% of oxygen, 23.5% of nitrogen, 1.2% of carbon dioxide gas, and 0.5% of carbon monoxide. The gaseous mixture of reaction products was cooled in a shell-tubular, heat-exchanger with water and brine in three cooling steps: 150° C in the first step; 40° C in the second step and 5° C in the third step. As a result, gaseous components containing 0.5% of isobutylene, 6.4% of methacrolein, 0.06% of methacrylic acid, 4.1% of water, 6.7% of oxygen, 76.5% of nitrogen, 3.9% of carbon dioxide gas, and 1.5% of carbon monoxide and liquefied components containing 0.6% of methacrolein, 1.3% of methacrylic acid and 97.9% of water, were obtained. The gaseous components did not form a detonating gas because the methacrolein components were highly diluted with the nitrogen diluent. The gaseous components were counter-currently contacted with water in an absorption tower(Rasching rings filled; 3 atm of inner pressure; 5° C) at a ratio of 78 moles of water to 1 mole of methacrolein. From the top of the absorption tower, a gas containing 0.6% of isobutylene, 7.5% of oxygen and 85.7% of nitrogen was obtained and from the bottom of the absorption tower, a solution containing 4.0% of methacrolein and 95.8% of water was obtained. The solution was distilled to obtain methacrolein containing about 29.4% of water. On the other hand, a 22% aqueous solution of lithium chloride was added to the liquefied components in a mixing vessel and the mixture was stirred and fed to a separating funnel for separation. The upper phase liquid contained 6.0% of methacrolein, 60.8% of methacrylic acid and 32.9% of water. The lower phase liquid contained 0.2% of methacrolein, 0.2% of methacrylic acid, 90.6% of water and 8.8% of lithium chloride. The upper phase liquid was fed to a distillation tower, to obtain methacrolein containing 29.4% of water from the top and crude methacrylic acid containing 33% of water from the bottom. The lower phase liquid was distilled in a distillation tower to obtain a methacrolein fraction (59.7% of methacrolein and 25.8% of water) and a methacrylic acid fraction (5.0% of methacrylic acid and 95.0% of water) from the top and a residual solution containing 9.2% of lithium chloride and 90.7% of water from the bottom. The residual solution was fed to a concentrating vessel to obtain a concentrated slurry containing 22% of lithium chloride and 77.7% of water. The slurry was recycled and fed to the mixing vessel. The methacrolein fractions obtained from each of the distillation towers were mixed and were recycled as starting materials in the second oxidation step. The resulting crude methacrylic acid was purified by a distillation to obtain methacrylic acid having a purity of 97 – 99% in substantially anhydrous condition.

EXAMPLE 2

The gaseous mixture of reaction products obtained in the first and second oxidation steps of Example 1 was cooled to 150° C by the heat-exchanger of Example 1, and was fed to an absorption tower filled with Raschig rings to be contacted with water at a ratio of 351 moles of water to 1 mole of methacrolein. The absorbed solution contained 0.28% of methacrolein, 0.10% of methacrylic acid and 99.62% of water. The solution was remarkably higher than that of Example 1.

EXAMPLE 3

The process of Example 1 was repeated except that the gaseous mixture of reaction products obtained in the first and second oxidation steps of Example 1 was indirectly cooled by the shell-tubular type heat-exchanger to 20° C to separate the mixture into gaseous components and liquefied components. As a result, the fraction of methacrylic acid was decreased by about 20% as compared with Example 1.

COMPARATIVE TEST

1. In the process of Example 1, the amount of oxygen in the second oxidation step and the convention of methacrolein was varied. The respective reaction products in the second oxidation step were mixed with the reaction products in the first oxidation step and the resulting mixture was cooled by the same apparatus under the same conditions as above to separate it into gaseous components and liquefied components. A part of the gaseous components discharged from the cooling apparatus was sampled and was fed to an explosion tester, wherein the gaseous components were tested to confirm the formation of an explosive gas by fusing a platinum resistance wire to ignite the explosion. The critical points of conversion of methacrolein (%) for preventing formation of an explosive gas relative to the amount of oxygen (moles) used in the second oxidation step were measured. The results are shown in above-mentioned Table 2.

2. Also, in the process of Example 1, the amount of oxygen in the second oxidation step and the conversion of methacrolein were varied, and only the reaction products in the second oxidation step were cooled by the same apparatus under the same conditions without mixing the reaction products in the first and second oxidation steps. The gaseous components were tested by the same method to confirm the formation of an explosive gas. The critical points of conversion of methacrolein (%) for preventing formation of an explosive gas relative to the amounts of oxygen (moles) in the second oxidation step were measured. The results are shown in above-mentioned Table 1.

3. In the process of (1), the conversion of isobutylene in the first oxidation step was decreased to 80% and the relationship between the critical points of conversion of methacrolein (%) for preventing formation of an explosive gas and the amounts of oxygen (moles) in the second oxidation step were measured by the same method. The results are shown in Table 3.

TABLE 3

| Amount of oxygen (moles) | Conversion of methacrolein required for preventing formation of an explosive gas (%) |
| --- | --- |
| 1 | > 42 |
| 1.25 | > 54 |
| 1.5 | > 66 |
| 1.75 | > 82 |

Having now fully described the invention, it will be apparent to one of ordinary skill in the art that many changes and modifications can be made thereto without departing from the spirit or scope of the invention as set forth herein.

What is claimed a new and intended to be covered by Letters Patent is:

1. A process for producing methacrylic acid by an oxidation procedure, which comprises:
    oxidizing isobutylene in a feed gas at a temperature of 200°–500° C and a pressure of 0.5 to 10 atm over a metal oxide oxidation catalyst suitable for oxidizing isobutylene to methacrolein at a contact time of 0.1–20 seconds in the presence of oxygen as the oxidizing agent and nitrogen as a gaseous diluent, wherein the amount of diluent gas in the feed gas ranges from 50–97 mole percent and wherein the molar ratio of molecular oxygen to isobutylene ranges from 1/3–4/1, such that a methacrolein containing reaction effluent is obtained in which the conversion of said isobutylene is greater than 80%;

simultaneously oxidizing methacrolein in a feed gas over an oxidation catalyst selected from the group consisting of metal oxides, phosphomolybdic acid, and ammonium, bismuth, antimony, potassium, cesium and thallium salts of phosphomolybdic acid, which is suitable for oxidizng methacrolein to methacrylic acid in the presence of oxygen as the oxidizing agent and nitrogen and stream as a gaseous diluent under the reaction conditions specified above for the oxidation of isobutylene, wherein the amounts of said diluent gas and said steam in said feed gas range from 50–97 mole percent and 5–90 mole percent respectively and wherein the amount of oxygen relative to 1 mole of methacrolein ranges from 1.2 to 2.0 moles, so that a methacrylic acid containing reaction effluent is obtained in which the conversion of methacrolein is 40% to less than 80%;

combining both of said reaction effluents;

effecting separation and isolation of methacrolein and methacrylic acid from the combined effluents, wherein the combined effluents are of such a resultant composition that the danger of the formation of an explosive gaseous mixture derived from the oxidation processes in the isolation and separation steps is eliminated; and returning the isolated methacrolein to the methacrolein oxidation step.

2. The process for producing methacrylic acid of claim 1, wherein the mixture of the reaction products obtained in the isobutylene oxidation and methacrolein oxidation steps is indirectly cooled to separate out a gas phase and a liquid phase, the gas phase is contacted with water to form a solution, and methacrolein and methacrylic acid are separated and recovered by distilling the solution and the liquid phase.

3. The process for producing methacrylic acid of claim 1 wherein said mixture is cooled to a temperature within the range of 1° – 50° C.

4. The process for producing methacrylic acid of claim 2 wherein said liquid phase is extracted with an agent for removing water therefrom prior to said distilling.

5. The process for producing methacrylic acid of claim 2, wherein the mixture of the reaction products obtained in the isobutylene oxidation and methacrolein oxidation steps is cooled in several steps.

6. The process for producing methacrylic acid of claim 1, wherein the reaction products obtained in the isobutylene oxidation and methacrolein oxidation steps are mixed, the mixture is contacted with water and the resulting solution is distilled to separate methacrolein and methacrylic acid.

7. The process for producing methacrylic acid of claim 1, wherein the mole ratio of oxygen to isobutylene in the gas feed in the isobutylene oxidation step is in the range of 1/1–3/1, and the molar ratio of oxygen to methacrolein in the feed gas in the methacrolein oxidation step is in the range of 1.2/1–2.0/1.

8. The process for producing methacrylic acid of claim 1, wherein the catalyst used in the isobutylene oxidation step is a metal oxide and the catalyst used in the methacrolein oxidation step is an ammonium, bismuth, antimony, potassium, cesium, rubidium or thallium salt of phosphomolybdic acid.

* * * * *